US012672796B2

(12) United States Patent
Bonev et al.

(10) Patent No.: US 12,672,796 B2
(45) Date of Patent: Jul. 7, 2026

(54) FALL RISK ASSESSMENT FOR A USER

(71) Applicant: Google LLC, Mountain View, CA (US)

(72) Inventors: Boyan Bonev, Sunnyvale, CA (US);
Jung Ook Hong, Sunnyvale, CA (US)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 18/725,415

(22) PCT Filed: Oct. 20, 2022

(86) PCT No.: PCT/US2022/047249
§ 371 (c)(1),
(2) Date: Jun. 28, 2024

(87) PCT Pub. No.: WO2023/129254
PCT Pub. Date: Jul. 6, 2023

(65) Prior Publication Data
US 2025/0098984 A1       Mar. 27, 2025

Related U.S. Application Data

(60) Provisional application No. 63/295,046, filed on Dec. 30, 2021.

(51) Int. Cl.
*A61B 5/11* (2006.01)
*A61B 5/00* (2006.01)
(Continued)

(52) U.S. Cl.
CPC .......... *A61B 5/1117* (2013.01); *A61B 5/4809* (2013.01); *A61B 5/4812* (2013.01);
(Continued)

(58) Field of Classification Search
CPC ... A61B 5/1117; A61B 5/4809; A61B 5/4812; A61B 5/4815; A61B 5/681;
(Continued)

(56) References Cited

U.S. PATENT DOCUMENTS 11,033,233 B2   6/2021   Hayes et al.
2011/0112442 A1   5/2011   Meger et al.
(Continued)

FOREIGN PATENT DOCUMENTS

JP   2007125368   5/2007
JP   2018198883   12/2018
(Continued)

OTHER PUBLICATIONS

Saidi et al., "Real-time Aging Friendly Fall Detection System", Proceedings of the 6th International Conference on Image and Signal Processing and their Applications (ISPA), Nov. 24-25, 2019, Mostaganem, Algeria, 6 pages.
(Continued)

*Primary Examiner* — Brian A Zimmerman
*Assistant Examiner* — Anthony D Afrifa-Kyei
(74) *Attorney, Agent, or Firm* — DORITY & MANNING P.A.

(57) ABSTRACT

A computer-implemented method for assessing a fall risk of a user is provided. The computer-implemented method includes obtaining data indicative of the user engaging in a fall risk activity. The computer-implemented method includes adjusting a fall detection threshold of a wearable computing device worn by the user based, at least in part, on the data indicative of the user engaging in the fall risk activity. The method includes providing a notification indicative of the user being at risk of falling due, at least in part, to the user engaging in the fall risk activity.

16 Claims, 10 Drawing Sheets

(51) Int. Cl.

| | |
|---|---|
| *G08B 21/04* | (2006.01) |
| *G16H 10/60* | (2018.01) |
| *G16H 40/67* | (2018.01) |
| *G01C 5/06* | (2006.01) |
| *G01P 13/00* | (2006.01) |

(52) U.S. Cl.

CPC ............ *A61B 5/4815* (2013.01); *A61B 5/681* (2013.01); *A61B 5/7267* (2013.01); *A61B 5/7275* (2013.01); *A61B 5/7405* (2013.01); *A61B 5/742* (2013.01); *G08B 21/043* (2013.01); *G16H 10/60* (2018.01); *G16H 40/67* (2018.01); *G01C 5/06* (2013.01); *G01P 13/00* (2013.01)

(58) Field of Classification Search

CPC ... A61B 5/7267; A61B 5/7275; A61B 5/7405; A61B 5/742; A61B 5/002; A61B 5/0205; A61B 5/024; A61B 5/02438; A61B 5/1112; A61B 5/1121; A61B 5/1123; A61B 5/6802; A61B 5/7246; A61B 5/7264; A61B 5/74; A61B 5/7455; A61B 5/746; A61B 5/747; A61B 2503/10; A61B 2560/0242; A61B 2562/0219; A61B 5/0002; A61B 5/00; A61B 5/0004; A61B 5/0015; A61B 5/0026; A61B 5/0031; A61B 5/0024; A61B 5/1118; A61B 5/165; A61B 5/486; A61B 5/6815; A61B 5/4824; A61B 5/4833; A61B 5/4884; A61B 5/6801; A61B 5/6831; G16H 40/67; G16H 10/60; G16H 80/00; G16H 20/30; G16H 40/63; G16H 50/30; G08B 21/043; G08B 21/02; G08B 21/04; G08B 21/0407; G08B 13/2454; G08B 21/0269; G08B 21/0446; G01C 5/06; G01C 21/12; G01P 13/00; G01P 15/00; G01S 19/13; G06F 1/1694; G06F 3/011; G06N 20/00; G06N 3/08

See application file for complete search history.

(56) References Cited

U.S. PATENT DOCUMENTS

| | | |
|---|---|---|
| 2013/0285813 A1 | 10/2013 | Kasama |
| 2014/0180621 A1 | 6/2014 | Poduri et al. |
| 2015/0226764 A1 | 8/2015 | Kate et al. |
| 2016/0038061 A1 | 2/2016 | Kechichian et al. |
| 2016/0220153 A1 | 8/2016 | Annegarn et al. |
| 2016/0267764 A1 | 9/2016 | Park et al. |
| 2019/0228633 A1* | 7/2019 | Tobiassen .......... G08B 21/0446 |
| 2020/0155039 A1 | 5/2020 | Forth et al. |
| 2020/0311609 A1 | 10/2020 | Pathak et al. |
| 2021/0020020 A1 | 1/2021 | Rothschild et al. |
| 2021/0049887 A1 | 2/2021 | Hansen et al. |
| 2021/0166554 A1 | 6/2021 | Kate |
| 2021/0349122 A1 | 11/2021 | Kechichian et al. |
| 2023/0000396 A1* | 1/2023 | Coffey .................. A61B 5/1117 |
| 2025/0046172 A1 | 2/2025 | Tan et al. |

FOREIGN PATENT DOCUMENTS

| | | |
|---|---|---|
| WO | WO 2016110804 | 1/2016 |
| WO | WO 2019098582 | 5/2019 |

OTHER PUBLICATIONS

International Search Report and Written Opinion for PCT/US22/47249, mailed on Feb. 7, 2023, 9 pages.

Zhou, "HeadsUp: Keeping Pedestrian Phone Addicts from Dangers Using Mobile Phone Sensors.", International Journal of Distributed Sensor Networks, Article ID 279846, 2015, 9 pages.

* cited by examiner

100

102

110

112

114

500

Obtain Data Associated with a Fall Risk Activity ⌐502

Adjust a Fall Detection Threshold Based, at Least in Part, on the Data ⌐504

Provide a Notification Indicative of the User Being at Risk of Falling ⌐506

Provide Data from One or More Sensors of Wearable Computing Device as an Input to a Machine-Learned Model — 602

Process the Data from the Sensor(s) in the Machine-Learned Model — 604

Output an Adjusted Fall Detection Threshold — 606

700

Obtain Sleep Data for a Sleep Event Associated with a User ⌐702

Obtain Data Indicative of User Taking Initial Steps After Waking ⌐704

Adjust Fall Detection Threshold Based on Sleep Data and Data Indicative of Initial Steps ⌐706

Provide a Notification Indicative of the User Being at Risk of Falling ⌐708

1

FALL RISK ASSESSMENT FOR A USER

PRIORITY CLAIM

This application is based upon and claims the right of priority under 35 U.S.C. § 371 to International Application No. PCT/US2022/047249 filed on Oct. 20, 2022, which claims priority to U.S. Patent Application No. 63/295,046, titled "Fall Risk Assessment for a User Wearing a Wearable Computing Device," having a filing date of Dec. 30, 2021. Applicant claims priority to and the benefit of each of such applications and incorporate all such applications herein by reference in their entirety.

FIELD

The present disclosure relates generally to wearable computing devices. More particularly, the present disclosure relates to methods for assessing a fall risk of a user wearing one or more wearable computing devices.

BACKGROUND

A wearable computing device can be worn, for instance, on a user's wrist. The wearable computing device can include one or more sensors (e.g., accelerometer, gyroscope, etc.) that can obtain data indicative of movement of the user. The data obtained from the one or more sensors can, in some instances, indicate occurrence of a fall event in which the user falls to the ground. The wearable computing device can, in some instances, alert emergency personnel in response to detecting the fall event.

SUMMARY

Aspects and advantages of embodiments of the present disclosure will be set forth in part in the following description, or can be learned from the description, or can be learned through practice of the embodiments.

In one aspect, a computer-implemented method for assessing a fall risk of a user is provided. The method includes obtaining data indicative of the user engaging in a fall risk activity. The method includes adjusting a fall detection threshold of a wearable computing device worn by the user based, at least in part, on the data indicative of the user engaging in the fall risk activity. The method includes providing a notification indicative of the user being at risk of falling due, at least in part, to the user engaging in the fall risk activity.

In some implementations, obtaining a signal from a mobile computing device associated with the user. The signal can be indicative of the user engaging in the fall risk activity. Furthermore, in such implementations, providing the notification for display on a display screen of the mobile computing device.

In some implementations, obtaining data indicative of the fall risk activity includes obtaining data from one or more sensors of the wearable computing device worn by the user.

In some implementations, adjusting the fall detection threshold of the wearable computing device includes providing the data from the one or more sensors of the wearable computing device as an input to a machine-learned model configured to process the data from the one or more sensors of the wearable computing device to determine an adjusted fall detection threshold. Furthermore, adjusting the fall detection threshold of the wearable computing device includes obtaining the adjusted fall detection threshold as an output of the machine-learned model.

In some implementations, the one or more sensors of the wearable computing device includes a plurality of different sensors and the adjusted fall detection threshold includes a plurality of adjusted fall detection thresholds. Furthermore, each of the plurality of adjusted fall detection thresholds is associated with a respective sensor of the plurality of different sensors.

In some implementations, the fall risk activity includes walking after waking from a sleep event. Furthermore, in such implementations, the data indicative of the user engaging in the fall risk activity includes motion data indicative of the user walking immediately following waking from the sleep event at a pace that exceeds a threshold pace.

In some implementations, the computer-implemented method includes obtaining sleep data associated with the sleep event. Furthermore, in such implementations, the computer-implemented method includes adjusting the fall detection threshold of the wearable computing device according to the sleep data and the motion data.

In some implementations, the sleep data includes at least one of a duration of the sleep event or a depth of the sleep event. Furthermore, the sleep data indicative of the depth of the sleep event indicates whether the user is waking from a rapid-eye-movement (REM) sleep cycle or a non-REM sleep cycle.

In some implementations, obtaining data indicative of the user engaging in the fall risk activity includes obtaining first data from one or more sensors of a first wearable computing device worn at a first location on a body of the user and obtaining second data from one or more sensors of a second wearable computing device worn at a second location on the body of the user. The second location on the body can be different from the first location on the body. Furthermore, in such implementations, adjusting the fall detection threshold of the wearable computing device includes adjusting the fall detection threshold of at least one of the first wearable computing device or the second wearable computing device.

In another aspect, a wearable computing device is provided. The wearable computing device includes a plurality of sensors. The wearable computing device further includes one or more processors communicatively coupled to the plurality of sensors. The one or more processors are configured to obtain data indicative of a user wearing the wearable computing device engaging in a fall risk activity. The one or more processors are further configured to adjust a fall detection threshold of the wearable computing device based, at least in part, on the data indicative of the user engaging in the fall risk activity. The one or more processors are further configured to provide a notification indicative of the user being at risk for falling due, at least in part, to the user engaging in the fall risk activity.

In yet another aspect, a non-transitory computer-readable medium storing instructions that, when executed by one or more processors, cause the one or more processors to perform operations is provided. The operations include obtaining data indicative of a user wearing a wearable computing device engaging in a fall risk activity. The operations include adjusting a fall detection threshold of the wearable computing device based, at least in part, on the data indicative of the user engaging in the fall risk activity. The operations include providing a notification indicative of the user being at risk of falling due, at least in part, to the user engaging in the fall risk activity.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which.

DETAILED DESCRIPTION

Figure 1:
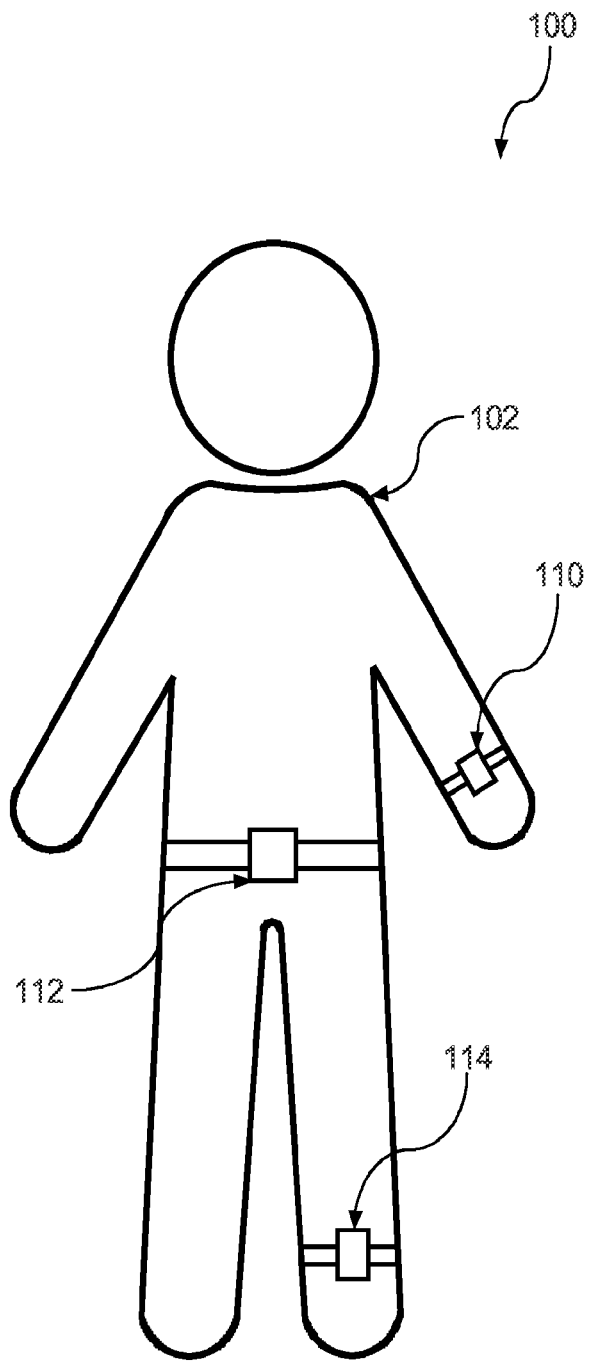
FIG. 1 depicts a user wearing multiple wearable computing devices according to some implementations of the present disclosure.

Reference now will be made in detail to embodiments of the present disclosure, one or more examples of which are illustrated in the drawings. Each example is provided by way of explanation of the present disclosure, not limitation of the present disclosure. In fact, it will be apparent to those skilled in the art that various modifications and variations can be made in the present disclosure without departing from the scope or spirit of the disclosure. For instance, features illustrated or described as part of one embodiment can be used with another embodiment to yield a still further embodiment. Thus, it is intended that the present invention covers such modifications and variations as come within the scope of the appended claims and their equivalents.

Example aspects of the present disclosure are directed to a wearable computing device that can be worn, for instance, on a user's wrist. The wearable computing device can include one or more sensors (e.g., accelerometers, gyroscopes, etc.) configured to obtain data indicative of motion of the user. The wearable computing device can generate a notification (e.g., visual, auditory, etc.) in response to the one or more sensors obtaining data indicative of motion corresponding to a fall event. For instance, the notification can include a text notification displayed on a display screen of the wearable computing device. Additionally, in some instances, the wearable computing device can notify emergency personnel in the event the user fails to take some action (e.g., dismiss notification).

Example aspects of the present disclosure are directed to fall risk prevention for a user wearing a wearable computing device. Fall risk prevention can include detecting the user is engaging in a fall risk activity. Fall risk prevention further includes adjusting a fall detection threshold in response to detecting the user is engaging in the fall risk activity. For example, the fall detection threshold can be adjusted (e.g., lowered) so that fall detection is more sensitive while the user is engaging in the fall risk activity. Additionally, fall risk prevention further includes notifying the user of the increased fall risk due, at least in part, to the user engaging in the fall risk activity. As used herein, the "fall detection threshold" can refer to a fall indicating parameter output by one or more fall detection devices. Furthermore, a fall event may be detected when the fall indicating parameter exceeds the fall detection threshold. It should be understood that the one or more fall detection devices can include any suitable device configured to detect motion of the user that is indicative of the fall event or motion that is indicative of an imminent fall event. For instance, in some implementations, the one or more fall detection devices can include one or more motion sensors (e.g., accelerometer, gyroscope). Alternatively, or additionally, the one or more fall detection devices can include a barometer.

In some implementations, the fall risk activity can include walking while viewing a display of a mobile computing device (e.g., smartphone). In such implementations, the mobile computing device can detect that the user is engaging in the fall risk activity and can communicate data indicative of the user engaging in the fall risk activity to the wearable computing device. Furthermore, the wearable computing device can adjust (e.g., lower) the fall detection threshold according to the fall risk activity in which the user is engaging. For instance, the wearable computing device can lower the fall detection threshold by a first amount in response to determining the user is engaging in a first fall risk activity. Conversely, the wearable computing device can lower the fall detection threshold by a second amount that is different from the first amount in response to determining the user is engaging in a second fall risk activity that is different than the first fall risk activity.

In some implementations, the wearable computing device can notify the user of their increased fall risk due to the user engaging in the fall risk activity. For instance, the wearable computing device can generate a notification (e.g., auditory, visual) indicative of the user's fall risk while engaging in the fall risk activity. In some implementations, the notification can be communicated to the mobile computing device and displayed on the display screen of the mobile computing device.

In some implementations, the fall risk activity can include carrying an object (e.g., a box, a drink, etc.) that requires a user to use both hands to support the object. For instance, one or more sensors (e.g., accelerometer) can obtain motion data indicative of the user walking without swinging their arms. In this manner, the wearable computing device can determine the user is engaging in the fall risk activity (e.g., carrying an object). Furthermore, the fall detection threshold can be adjusted (e.g., lowered) while the motion data indicates the user is engaging in the fall risk activity.

In some implementations, the wearable computing device can generate a notification indicative of the user engaging in the fall risk activity (e.g., carrying an object). For instance, in some implementations, the wearable computing device can include a haptic feedback device (e.g., piezoelectric buzzer) configured to provide haptic feedback (e.g., vibrate) to prompt the user to set the object down and read a notification provided on a display screen of the wearable computing device and indicative of the fall risk activity. In alternative implementations, the wearable computing device can emit an auditory notification (e.g., computer-generated voice) indicative of the fall risk activity.

In some implementations, the fall risk activity can include walking after waking from a sleep event. The risk of falling within the first few steps after waking from the sleep event can vary based on various parameters (e.g., time spent sleeping, depth of sleep, movement before taking first steps, pace of first steps). For example, a user that walks immediately after waking from the sleep event can be more susceptible to a fall event compared to a user that waits a period of time before walking after waking from the sleep event.

As another example, a duration of the sleep event can impact the likelihood of a fall event occurring within the first few steps taken after waking from the sleep event. For instance, a user waking up from a sleep event lasting several hours can be more susceptible to a fall-event compared to a user waking from a sleep event of a shorter duration (e.g., an hour or less). The depth of the sleep event can also affect the likelihood of the user falling within the first steps taken after waking from the sleep event. For example, a user waking from a deeper sleep event (e.g., including one or more rapid eye movement (REM) sleep cycles) can be more susceptible to a fall-event compared to a user waking from a lighter sleep event (e.g., including a non-REM sleep cycle).

As yet another example, a pace at which the user walks after waking from the sleep event can affect the fall risk. For instance, the user can be more susceptible to a fall-event when the user walks quickly (e.g., above a threshold cadence) immediately after waking from the sleep event. Conversely, the user can be less susceptible to a fall event when the user walks slowly (e.g., below the threshold cadence) immediately after waking from the sleep event.

In some implementations, the fall detection threshold can be adjusted (e.g. lowered) according, at least in part, to the one or more of the parameters discussed above. For example, the fall detection threshold can be lowered more for a user waking from a deep sleep event (e.g., REM cycle) than for a user waking from a light sleep event (e.g., non-REM cycle) since the user waking from the deep sleep event is likely less alert than the user waking from the light sleep event and is therefore more susceptible to falling. As another example, the fall detection threshold can be lowered more for a user waking from a sleep event lasting several hours compared to a user waking from a sleep event (e.g., nap) lasting a shorter duration since the user waking from the longer sleep event is more susceptible to falling than the user waking from the shorter sleep event. As yet another example, the fall detection threshold can be lowered more for a user that walks immediately after waking compared to a user that waits a threshold amount of time after waking from the sleep event before walking.

In some implementations, the fall risk activity can include walking when fatigued. For instance, one or more sensors (e.g., accelerometer, gyroscope, etc.) can obtain motion data indicative of the user engaging in an exercise event (e.g., running, lifting, swimming, cycling, etc.). The risk of the user falling while walking after engaging in the exercise event can vary based on various parameters. For instance, the type of exercise event the user engages in can affect the likelihood of the user falling when walking after completing the exercise event. As an example, the fall risk for a user walking after completing a run workout can be different than the fall risk for the user after completing a swim workout.

In some implementations, the fall detection threshold can be adjusted (e.g., lowered) according, at least in part, to a duration of an exercise event. For instance, the fall detection threshold can be lowered more for a user after completing a first exercise event of a first duration than for the user after completing a second exercise event of a second duration that is shorter than the first duration.

In some implementations, an adjusted fall detection threshold for detecting a fall-event while the user is engaging in a fall risk activity can be determined using a machine-learned model (e.g., convolution neural network). For instance, data from one or more sensors (e.g., accelerometer, gyroscope, barometer) can be provided as an input to the machine-learned model. The machine-learned model can process the data from the one or more sensors to determine the adjusted fall detection threshold. Furthermore, in some implementations, the adjusted fall detection threshold can be provided as an input to a classifier model configured to classify the adjusted fall detection threshold as one of a plurality of fall risk activities. In this manner, the one or more machine-learned models can learn the different fall risk activities and the different adjusted fall detection thresholds associated with each of the different fall risk activities.

Wearable computing devices, systems, and methods according to example aspects of the present disclosure can provide numerous technical effects and benefits. For instance, a wearable computing device can detect that the user is engaging in a fall risk activity and adjust (e.g., lower) a fall detection threshold while the user is engaging in the fall risk activity. In this manner, the wearable computing device can be more likely to detect a fall-event due to the user engaging in the fall risk activity. Additionally, the wearable computing device can provide a notification of the user being at risk for a fall-event due, at least in part, to the user engaging in the fall risk activity. In this manner, the wearable computing device can educate the user on his or her susceptibility to a fall-event while engaging in the fall risk activity.

Figure 2:
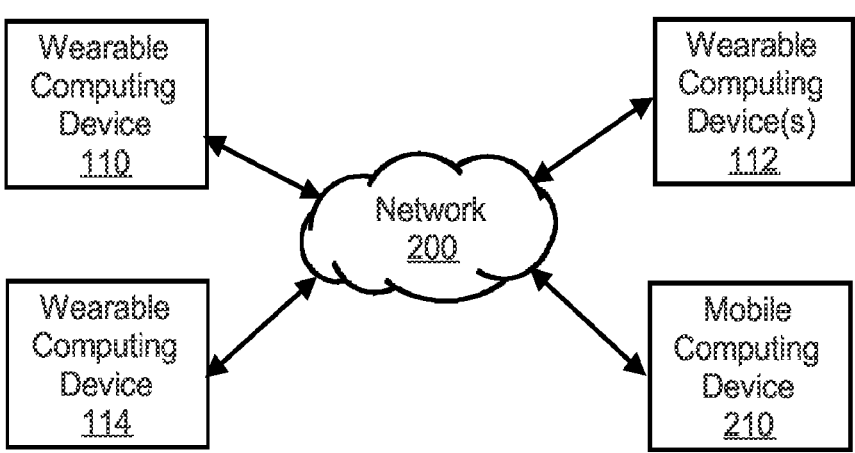
FIG. 2 depicts a network for communicating between wearable computing devices worn by the user according to some implementations of the present disclosure.

Referring now to the FIGS., FIGS. 1 and 2 depict a system 100 for assessing a fall risk of a user 102 is provided according to some implementations of the present disclosure. The system 100 can include one or more wearable computing devices. For instance, in some implementations, the system can include a first wearable computing device 110 worn on an upper extremity (e.g., wrist) of the user 102, a second wearable computing device 112 worn on a waist of the user 102, and a third wearable computing device 114 worn on a lower extremity (e.g., ankle) of the user 102.

It should be understood that the system 100 can include more or fewer wearable computing devices than what is shown in FIG. 1. For instance, in some implementations, the system 100 can include only a wearable computing device that is worn on the wrist of the user 102, such as the second wearable computing device 112. It should also be understood that the system 100 can include wearable computing devices that can be worn at other locations than those shown in FIG. 1. For instance, in some implementations, the system 100 can include a wearable computing device (e.g., earpiece) that can be worn in an ear of the user 102. Alternatively, or additionally, the system 100 can include a wearable computing device worn on a head of the user 102. For instance, in some implementations, the wearable computing device worn on the head of the user 102 can include a pair of glasses. In some implementations, the system 100 can include a wearable computing device worn on a foot of the user 102.

In some implementations, the wearable computing devices 110, 112, 114 can be communicatively coupled to one another via a communications network 200. In this manner, the wearable computing devices 110, 112, 114 can communicate with one another via the communications network 200. Furthermore, in some implementations, one or more of the wearable computing devices 110, 112, 114 can be communicatively coupled to a mobile computing device 210 via the communications network 200. Examples of the mobile computing device 210 can include, for instance, a smartphone, a tablet, or a laptop. It should be understood that the mobile computing device 210 can include any handheld electronic device having a display screen. In some implementations, the wearable computing devices 110, 112, 114 can be configured to communicate data over the communications network 200 to a server (not shown). For instance, in some implementations, the wearable computing device 110, 112, 114 can be configured to communicate the data to the server via the mobile computing device 210. Stated another way, the wearable computing devices 110, 112, 114 can communicate the data over the communications network 200 to the mobile computing device 210 and the mobile computing device 210 can communicate the data to the server via the communications network 200 or a different communications network (e.g., the Internet).

It should also be understood that the communication network 200 can be any type of communications network, such as a local area network. In general, communication over the communications network 200 can be carried via any type of wireless connection, using a wide variety of communication protocols, encodings, or formats and/or protection schemes (e.g., VPN, secure HTTP, SSL).

Figure 3:
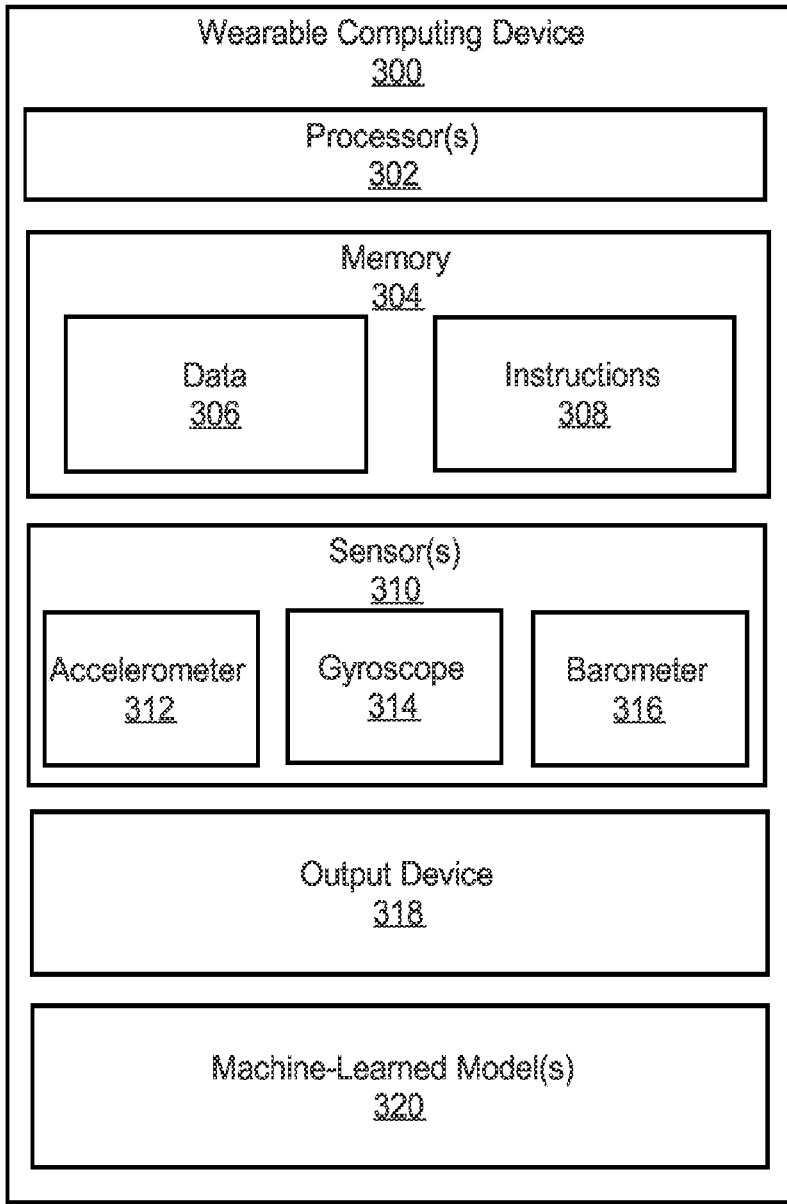
FIG. 3 depicts a block diagram of components of a wearable computing device according to some implementations of the present disclosure.

Referring now to FIG. 3, a block diagram of components of a wearable computing device 300 is provided according to some implementations of the present disclosure. It should be understood that the wearable computing device 300 can be implemented within the system 100 discussed above with reference to FIGS. 1 and 2. For instance, the wearable computing device 300 can be one of the wearable computing devices 110, 112, 114 worn by the user 102.

As shown, the wearable computing device 300 can include one or more processors 302. The one or more processors 302 can include any suitable processing device (e.g., a processor core, a microprocessor, an application specific integrated circuit (AISC), a field programmable gate array (FPGA), a microcontroller, etc.). The wearable computing device 300 can further include a memory 304. The memory 304 can include one or more non-transitory computer-readable storage media, such as random access memory (RAM), read-only memory (ROM), electronically erasable programmable ready-only memory (EEPROM), erasable programmable read-only memory (EPROM), flash memory devices, and combinations thereof. The memory 304 can store data 306 and instructions 308 that, when executed by the one or more processors 302, cause the one or more processors 302 to perform operations disclosed herein.

The wearable computing device 300 can include a plurality of sensors 310. For instance, in some implementations, the plurality of sensors 310 can include an accelerometer 312 (e.g., a multi-axis accelerometer) and a gyroscope 314. In this manner, the accelerometer 312, the gyroscope 314, or both can obtain motion data (e.g., acceleration, angular velocity) indicative of movement of the user 102 (FIG. 1). For instance, in some implementations, the motion data can be indicative of the user engaging in a fall risk activity (e.g., carrying an object, walking after waking from a nap, etc.). Additionally, in some implementations, the plurality of sensors 310 can further include a barometer 316. The barometer 316 can obtain pressure data indicative of a change in altitude. For instance, the barometer 316 can obtain pressure data indicative of a change in altitude that is associated with the user falling (e.g., a fall event).

In some implementations, the plurality of sensors 310 can include one or more biometric sensors. For instance, in some implementations, the one or more biometric sensors can include a photoplethysmogram (PPG) sensor. Alternatively, or additionally, the sensors 310 can include a temperature sensor configured to detect a body temperature of the user 102 (FIG. 1) wearing the wearable computing device 300. It should be understood that the scope of the present disclosure is not intended to cover wearable computing devices with biometric sensors other than the PPG sensor and body temperature sensor.

In some implementations, the wearable computing device 300 can include one or more output devices 318. For instance, the one or more output devices 318 can include a display screen. In this manner, the wearable computing device 300 can display content (e.g., notifications) that can be viewed by the user 102. Alternatively, or additionally, the one or more output devices 318 can include one or more speakers. In this manner, the wearable computing device 300 can emit audible noises (e.g., alarm, voice automated message, etc.) for the user 102. As will be discussed below, the wearable computing device 300 can be configured to assess a fall risk of the user 102.

In some implementations, the one or more processors 302 can be communicatively coupled to the plurality of sensors 310. For instance, the one or more processors 302 can be communicatively coupled to the plurality of sensors 310 via a data interface (e.g., data bus). In this manner, the one or more processors 302 can obtain data from the plurality of sensors 310. In some implementations, the one or more processors 302 can determine a fall risk activity in which the user 102 (FIG. 1) is engaging based, at least in part, on the data obtained from one or more of the sensors 310.

In some implementations, the one or more processors 302 of the wearable computing device 300 can adjust (e.g. lower) a fall detection threshold for detecting whether a fall event (e.g., the user of the wearable computing device falling) has occurred. More particularly, the one or more processors 302 can adjust the fall detection threshold of one or more one sensors 310 of the wearable computing device 300 based on the fall risk activity in which the user is engaging.

It should be understood that the one or more processors 302 can be configured to adjust the fall detection threshold differently depending on the fall risk activity in which the user 102 is engaging. For instance, the one or more processors 302 can be configured to lower the fall detection threshold by a first amount when the user is engaging in a first fall risk activity (e.g., walking after waking from a sleep event) and can be further configured to lower the fall detection threshold by a second amount that is different than the first amount when the user is engaging in a second fall risk activity (e.g., walking while carrying an object).

In some implementations, biometric data obtained from the one more biometric sensors (e.g., PPG sensor, temperature sensor) can indicate the user 102 is engaging in a fall risk activity. For instance, in some implementations, PPG data from the PPG sensor, temperature data obtained from the temperature, or both can indicate the user is engaging in a fall-risk activity, such as running. In such implementations, the fall detection threshold of one or more sensors 310 (e.g., accelerometer, gyroscope, barometer, etc.) on the wearable computing device 300 can be adjusted (e.g., lowered) in response to the data from the one or more biometric sensors on the wearable computing device 300 indicating the user is engaging in a fall-risk activity, such as running.

In some implementations, biometric data obtained from the one or more biometric sensors (e.g., PPG sensor, temperature sensor) of the wearable computing device 300 can indicate the user 102 is not engaging in a low risk activity (e.g., sitting). For instance, in some implementations, the biometric data can indicate the user 102 is sitting. In such implementations, the one or more processors 302 of the wearable computing device 300 can be configured to adjust (e.g., increase) the fall detection threshold of the wearable computing device 300 since the user 102 is engaging in the low risk activity.

In some implementations, biometric data obtained from the one or more biometric sensors of the wearable computing device 300 can indicate whether the wearable computing device 300 is currently being worn by the user 102. For instance, in some implementations, the biometric data obtained from the one or more biometric sensors can indicate the wearable computing device 300 is not being worn (e.g., off-wrist) by the user 102. In such implementations, the one or more processors 302 can be configured to disable fall-detection functionality while the biometric data indicates the wearable computing device 300 is not being worn by the user 102. In this manner, erroneous data from the one or more sensors 310 that is indicative of the user 102 engaging in a fall risk activity can be ignore. It should be understood that the one or more computing device 302 can be configured to enable fall-detection functionality when the biometric data indicates the wearable computing device 300 is being worn (e.g., on-wrist) by the user 102.

In some implementations, the wearable computing device 300 can include one or more machine-learned models 320. For instance, in some implementations, the one or more machine-learned models 320 can be stored in the memory 304 of the wearable computing device 300. In alternative implementations, the one or more machine-learned models 320 can be stored in the memory of one or more devices that are remote relative to the wearable computing device 300. For instance, in some implementations, the one or more machine-learned models 320 can be stored in memory of the mobile computing device 210 (FIG. 2) that is communicatively coupled with the wearable computing device 300 via the network 200. Alternatively, or additionally, the one or more machine-learned models 320 can be stored on one or more servers (not shown) that are communicatively coupled with the wearable computing device 300 via the network 200. As will now be discussed, the one or more machine-learned models 320 can be configured to adjust a fall detection threshold based, at least in part, on data obtained from one or more of the sensors 310.

Figure 4:
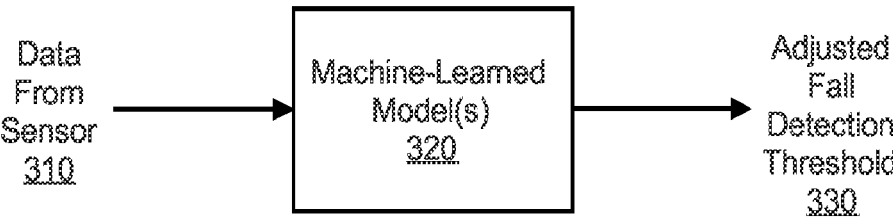
FIG. 4 depicts a block diagram of a machine-learned model for adjusting a fall detection threshold of a wearable computing device according to some implementations of the present disclosure

Referring now to FIG. 4, data from one or more of the sensors 310 can be provided as an input to the one or more machine-learned models 320. For instance, in some implementations, data from at least one of the accelerometer 312 (FIG. 3), the gyroscope 314 (FIG. 3), or the barometer 316 can be provided as an input to the one or more machine-learned models 320. The one or more machine-learned models 320 can process the data from the one or more sensors 310 to determine an adjusted fall detection threshold for a fall event. In some implementations, the output of the one or more machine-learned models 320 can be a single numerical value that can be used to determine whether a fall event has occurred. In alternative implementations, the output of the one or more machine-learned models 320 can include a plurality of outputs. Each of the plurality of outputs can correspond to a fall detection threshold for one or more of the sensors 310. For instance, a first output of the one or more machine-learned models 320 can correspond to a first fall detection threshold for the accelerometer 312. Conversely, a second output of the one or more machine-learned models 320 can correspond to a second fall detection threshold for the gyroscope 314. Still further, in some implementations, a third output of the one or more machine-learned models 320 can correspond to a third fall detection threshold for the barometer 316.

It should be understood that the one or more machine-learned models 320 can include any suitable type of machine-learned model. For instance, the one or more machine-learned models 320 can include, without limitation, a convolutional neural network, a decision tree, a Bayesian network, a support vector machine, a K-means cluster, or any other suitable type of machine-learned model.

Figure 5:
FIG. 5 depicts a flow diagram of a method for assessing a fall risk according to some implementations of the present disclosure.
Figure 5:
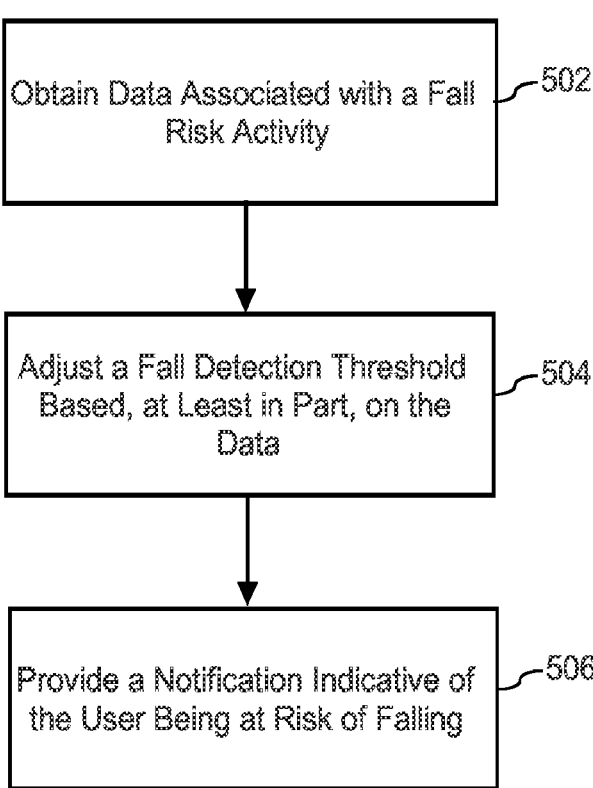

Referring now to FIG. 5, a flow diagram of an example method 500 of assessing a fall risk of a user wearable a wearable computing device is provided according to some implementations of the present disclosure. The method 500 may be implemented using, for instance, the wearable computing device 300 discussed above with reference to FIG. 3. FIG. 5 depicts steps performed in a particular order for purposes of illustration and discussion. Those of ordinary skill in the art, using the disclosures provided herein, will understand that various steps of the method 500 or any of the other methods disclosed herein may be adapted, modified, rearranged, performed simultaneously, or modified in various ways without deviating from the scope of the present disclosure.

At (502), the method 500 can include obtaining, by one or more processors of a wearable computing device worn by a user, data indicative of a user engaging in a fall risk activity. In some implementations, the data can be obtained from a mobile computing device (e.g., smartphone, tablet, etc.) associated with the user. For instance, the data can include a signal indicative of the user engaging in a fall risk activity (e.g., walking while viewing a display of the mobile computing device). In this manner, the mobile computing device can determine the user is engaging in a fall risk activity and can communicate data (e.g., a signal) to the wearable computing device that is indicative of the user engaging in the fall risk activity.

In alternative implementations, the data can be obtained from one or more sensors of the wearable computing device. For instance, an accelerometer of the wearable computing device can obtain acceleration data along one or more axes that is indicative of the user engaging in the fall risk activity. For instance, the acceleration data can indicate that the user is walking without swinging their upper-extremities, which can be indicative of the user holding an object (e.g., smartphone, tablet, box, etc.) while walking. Alternatively, or additionally, the data, in some implementations, can be obtained from one or more sensors of another wearable device worn by the user. For instance, the data can be obtained from one or more sensors of a wearable computing device worn, for instance, on a lower extremity (e.g., ankle) of the user.

At (504), the method 500 can include adjusting a fall detection threshold of the wearable computing device based, at least in part, on the data obtained at (502). For instance, in some implementations, the fall detection threshold can be lowered. In this manner, the wearable computing device can be more sensitive to detecting a fall event while the user is performing the fall risk activity.

In some implementations, adjusting the fall detection threshold of the wearable computing device can be a two-step process. For instance, in some implementations, adjusting the fall detection threshold of the wearable computing device can include providing the data obtained at (502) as an input to a first machine-learned model configured to classify the fall risk activity as one of a plurality of different fall risk activities (e.g., carrying a box, walking after waking from sleep, etc.). Stated another way, the machine-learned model can be configured to output a classification of the fall risk activity. For instance, in some implementations, the machine-learned model can be configured to output an identifier of whichever of the plurality of different fall risk activities the machine-learned model classifies the data obtained at (502) as being.

In some implementations the classification of the fall risk activity can be provided as an input to a second machine-learned model. The second machine-learned model can be configured to process the input to determine an adjusted fall detection threshold that is provided as an output of the second machine-learned model. For instance, in some implementations, the output can be a single adjusted fall detection threshold. In alternative implementations, the output can be a plurality of adjusted fall detection thresholds. Furthermore, in such implementations, each of the plurality of adjusted fall detection thresholds can be associated with a different sensor. For example, a first adjusted fall detection threshold can be associated with a first type of sensor (e.g., accelerometer) of the wearable computing device, whereas a second adjusted fall detection threshold can be associated with a second type of sensor (e.g., gyroscope, barometer) of the wearable computing device.

At (506), the method 500 can include providing a notification indicative of the user being at risk of falling due, at least in part, to the user engaging in the fall risk activity. For instance, in some implementations, the wearable computing device can include an output device (e.g., piezoelectric motor) that can vibrate to prompt the user to set the object down and read a notification provided on a display screen of the wearable computing device and indicative of the fall risk activity. In alternative implementations, the wearable computing device can emit an auditory notification (e.g., computer-generated voice) indicative of the fall risk activity.

Figure 6:
FIG. 6 depicts a flow diagram of a method for adjusting a fall detection threshold according to some implementations of the present disclosure.
Figure 6:
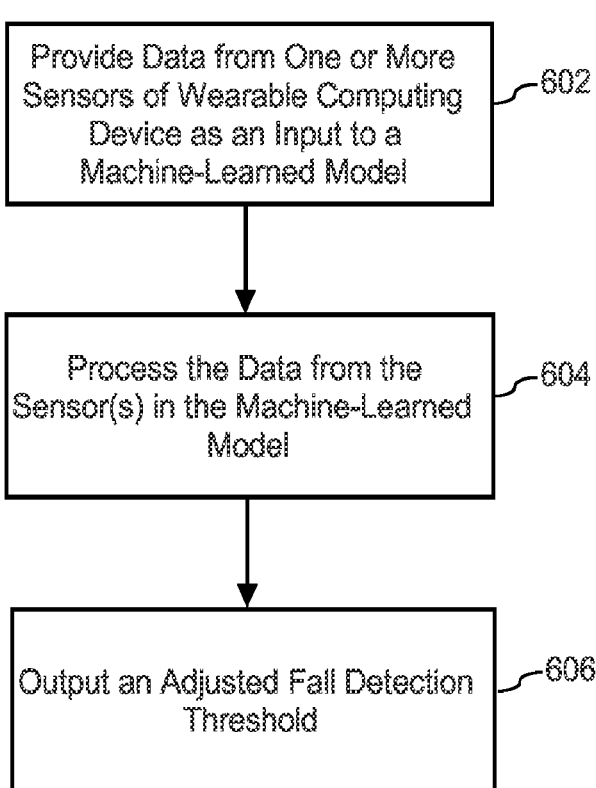

Referring now to FIG. 6, a flow diagram of an example method 600 of adjusting a fall detection threshold of a wearable computing device is provided according to some implementations of the present disclosure. The method 600 may be implemented using, for instance, the wearable computing device 300 discussed above with reference to FIG. 3. FIG. 6 depicts steps performed in a particular order for purposes of illustration and discussion. Those of ordinary skill in the art, using the disclosures provided herein, will understand that various steps of the method 600 or any of the other methods disclosed herein may be adapted, modified, rearranged, performed simultaneously, or modified in various ways without deviating from the scope of the present disclosure.

At (602), the method 600 can include providing data from one or more sensors of one or more wearable computing devices worn by a user can be provided as an input to a machine-learned model. For instance, in some implementations, acceleration data for a period of time can be provided as a first input to the machine-learned model. Furthermore, in some implementations, pressure data from a barometer of the one or more wearable computing devices can be provided as a second input to the machine-learned model. It should be understood that data from any suitable sensor of the one or more computing devices that can obtain data indicative of motion of the user can be provided as an input to the machine-learned model.

At (604), the method 600 can include processing the data input at (602) to determine an adjusted fall detection threshold. For instance, in some implementations, the adjusted fall detection threshold can be a single numerical value that can be used to determine whether motion of the user corresponds to a fall event. At (606), the method 600 can include outputting the adjusted fall detection threshold.

Figure 7:
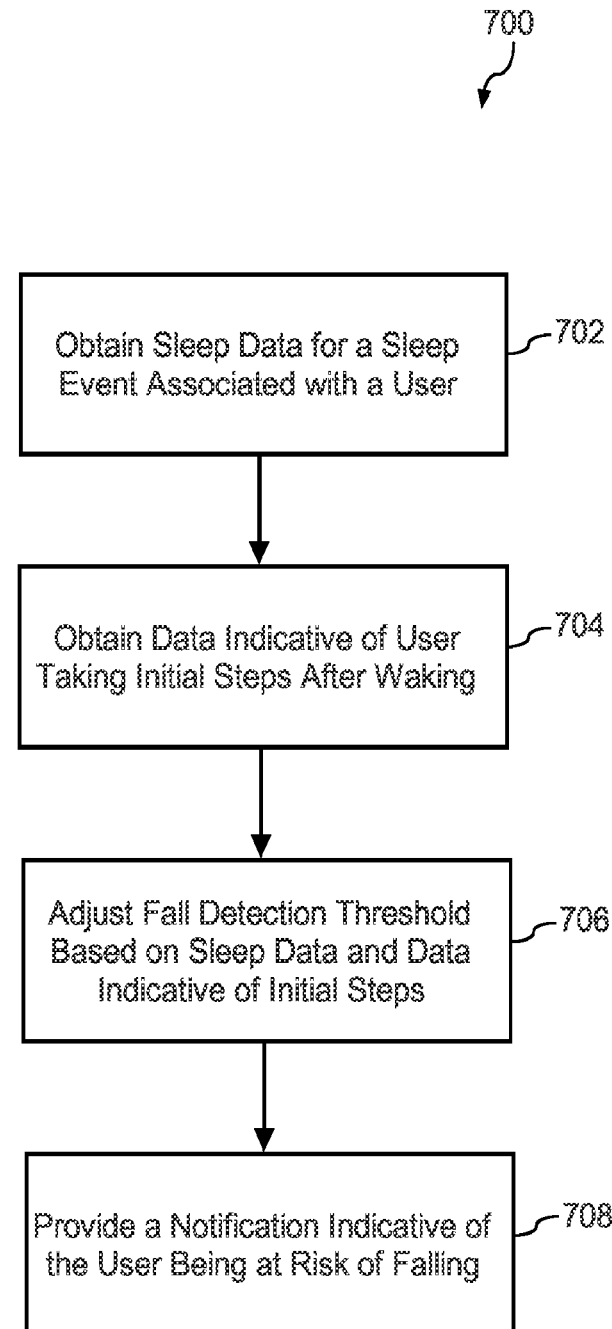
FIG. 7 depicts a flow diagram of a method for assessing a fall risk after waking from a sleep event according to some implementations of the present disclosure.

Referring now to FIG. 7, a flow diagram of another method of assessing a fall risk of a user wearable a wearable computing device is provided according to some implementations of the present disclosure. The method 700 may be implemented using, for instance, the wearable computing device 300 discussed above with reference to FIG. 3. FIG. 7 depicts steps performed in a particular order for purposes of illustration and discussion. Those of ordinary skill in the art, using the disclosures provided herein, will understand that various steps of the method 700 or any of the other methods disclosed herein may be adapted, modified, rearranged, performed simultaneously, or modified in various ways without deviating from the scope of the present disclosure.

At (702), the method 700 can include obtaining sleep data for a sleep event associated with a user wearing the wearable computing device. For instance, the sleep data can include a duration of the sleep event. Alternatively, or additionally, the sleep data can indicate a depth of the sleep event. For instance, the depth of the sleep event can indicate whether the user is waking from a deep sleep event (e.g., a REM sleep cycle) or a light sleep event (e.g., non-REM sleep cycle). It should be understood that the sleep data can include any data that is indicative of one or more metrics associated with the sleep event from which the user is waking.

At (704), the method 700 can obtain data indicative of the user engaging in a fall risk activity after waking from the sleep event. For instance, the fall risk activity can include walking after waking from the sleep event. In some implementations, the data can include data from one or more sensors of the wearable computing device that is indicative of the user walking. For instance, the data can include data indicative of a pace at which the user is walking.

At (706), the method 700 can include adjusting a fall detection threshold based on the sleep data obtained at (702) and the data obtained at (704) that is indicative of the user engaging in the fall risk activity. It should be understood that the fall detection threshold can be adjusted differently depending on the data obtained at (702) and (704). For example, the fall detection threshold can be adjusted (e.g. lowered) differently depending on the duration of the sleep event. In some implementations, the fall detection threshold can be lowered more for a user waking from a sleep event lasting several hours compared to a user waking from a shorter sleep event, such as a nap. In this manner, the wearable computing device can be more sensitive to detecting a fall event for the user waking from the sleep event lasting several hours compared to the user waking from the sleep event lasting a shorter duration.

In some implementations, the fall detection threshold can be adjusted (e.g., lowered) differently depending on the depth of the sleep event. For instance, the fall detection threshold can be lowered more for a user waking from a deep sleep event (e.g., a REM cycle) than for a user waking from a light sleep event (e.g., a non-REM cycle). In this manner, the wearable computing device can be more sensitive to detecting a fall event for the user waking from the deeper sleep event compared to the user waking from the lighter sleep event.

In some implementations, the fall detection threshold can be lowered more for a user that is walking at a pace that is greater than a threshold pace associated with walking after waking from the sleep event. In this manner, the wearable computing device can be more sensitive to detecting a fall event when the user is walking at a pace that exceeds the threshold pace.

At (708), the method 700 can include providing a notification indicative of the user being at risk of falling while walking after waking from the sleep event. For instance, in some implementations, the notification can include a visual notification provided via a display screen of the wearable computing device worn by the user. Alternatively, or additionally, the notification can include an auditory notification provided via a speaker of the wearable computing device worn by the user. In this manner, the notification (e.g., visual, auditory, or both) can prompt the user to walk in a more cautious manner (e.g., at a pace that is below a threshold pace associated with walking after waking from the sleep event).

Figure 8:
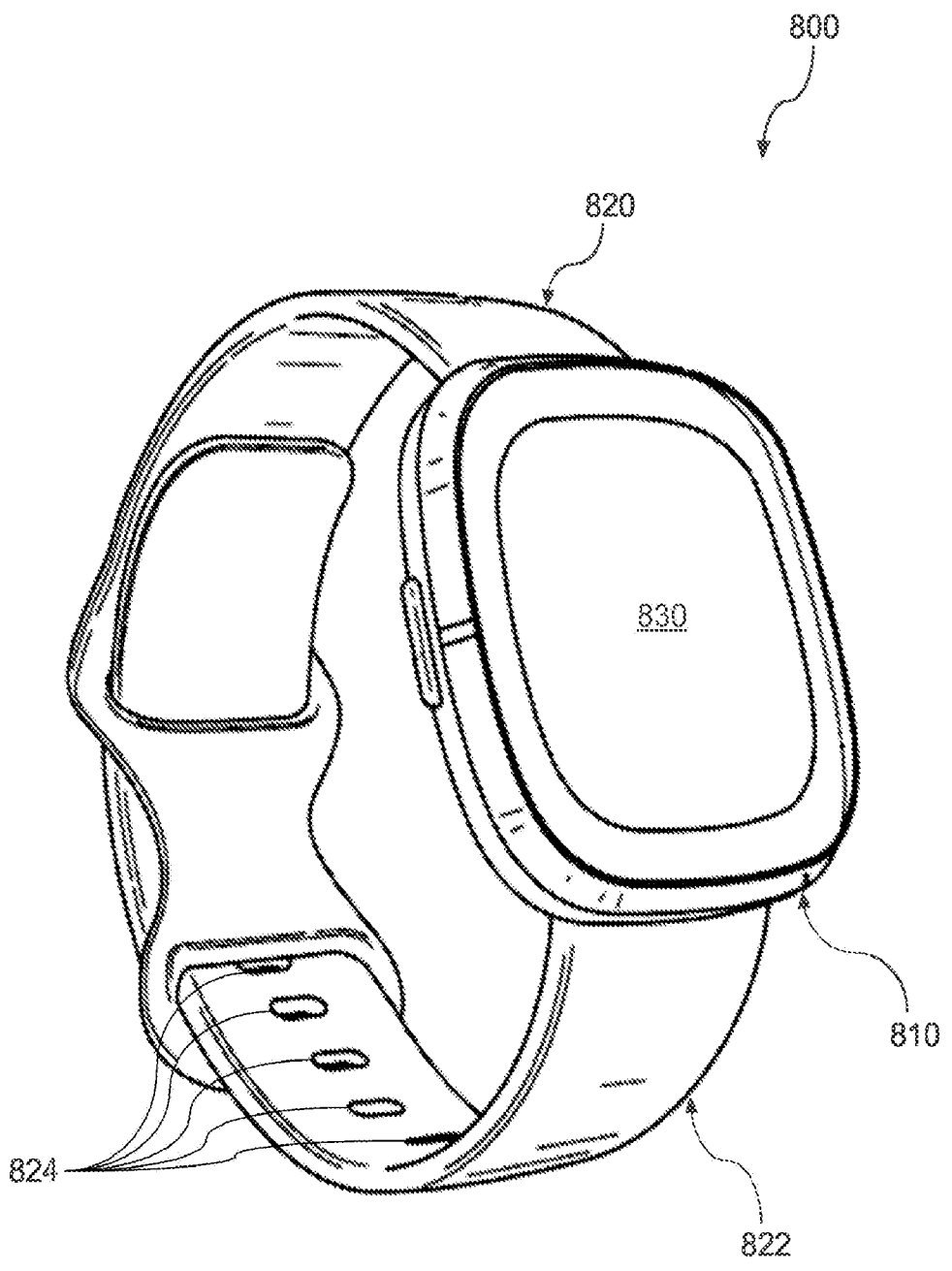
FIG. 8 depicts a front perspective view of a wearable computing device according to some implementations of the present disclosure.
Figure 9:
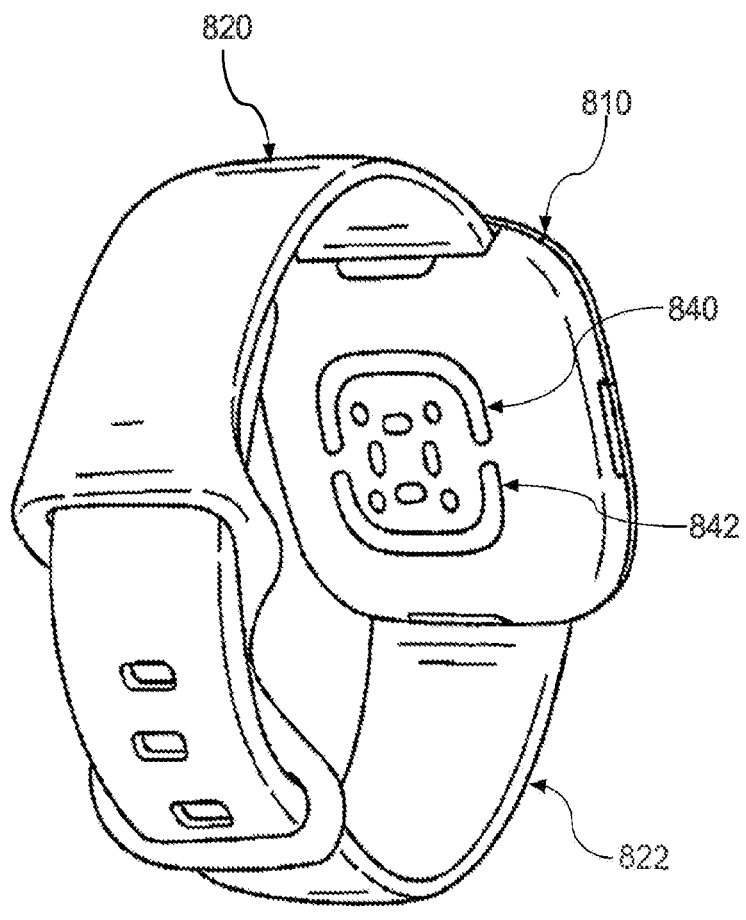
FIG. 9 depicts a rear perspective view of a wearable computing device according to some implementations of the present disclosure.

Referring now to FIGS. 8 and 9, a wearable computing device 800 according to some implementations of the present disclosure. As shown, the wearable computing device 800 can be worn, for instance, on an arm (e.g., wrist) of a user. For instance, the wearable computing device 800 can include a housing 810. The wearable computing device 800 can include one or more electronic components (e.g., disposed on printed circuit boards) disposed within the housing 810. Furthermore, the wearable computing device 800 can include a battery (not shown) that is disposed within the housing 810.

As shown, the wearable computing device 800 can include a first band 820 coupled to the housing 810 at a first location and a second band 822 coupled to the housing 810 at a second location. The first band 820 and the second band 822 can be coupled to one another to secure the housing 810 to the arm of the user. For instance, the first band 820 can include a buckle or clasp (not shown). Additionally, the second band 822 can define a plurality of apertures 824 spaced apart from one another along a length of the second band 822. In such implementations, a prong of the buckle associated with the first band 820 can extend through one of the plurality of openings defined by the second band 822 to couple the first band 820 to the second band 822.

It should be appreciated that the first band 820 can be coupled to the second band 822 using any suitable type of fastener. For instance, in some implementations, the first band 820 and the second band 822 can include a magnet. In such implementations, the first band 820 and the second band 822 can be magnetically coupled to one another to secure the housing 810 to the arm of the user.

In some implementations, the wearable computing device 800 can include a display 830 configured to display content (e.g., time, date, biometric, notifications, etc.) for viewing by the user. For instance, the display 830 can include a plurality of pixels. In some implementations, the display 830 can include an organic light emitting diode (OLED) display. It should be understood, however, that the display 830 can include any suitable type of display.

In some implementations, the wearable computing device 800 can include a first electrode 840 and a second electrode 842. It should be understood that the wearable computing device 800 can include more or fewer electrodes. As shown, the first electrode 840 and the second electrode 842 are positioned with respective apertures (e.g., cutouts) defined by the housing 810. Furthermore, the first electrode 840 and the second electrode 842 can each contact (e.g., touch) the wrist of the user. In this manner, the first electrode 840 and the second electrode 842 can be used to measure one or more biometrics (e.g., electrodermal activity, electrocardiogram) of the user.

Figure 10:
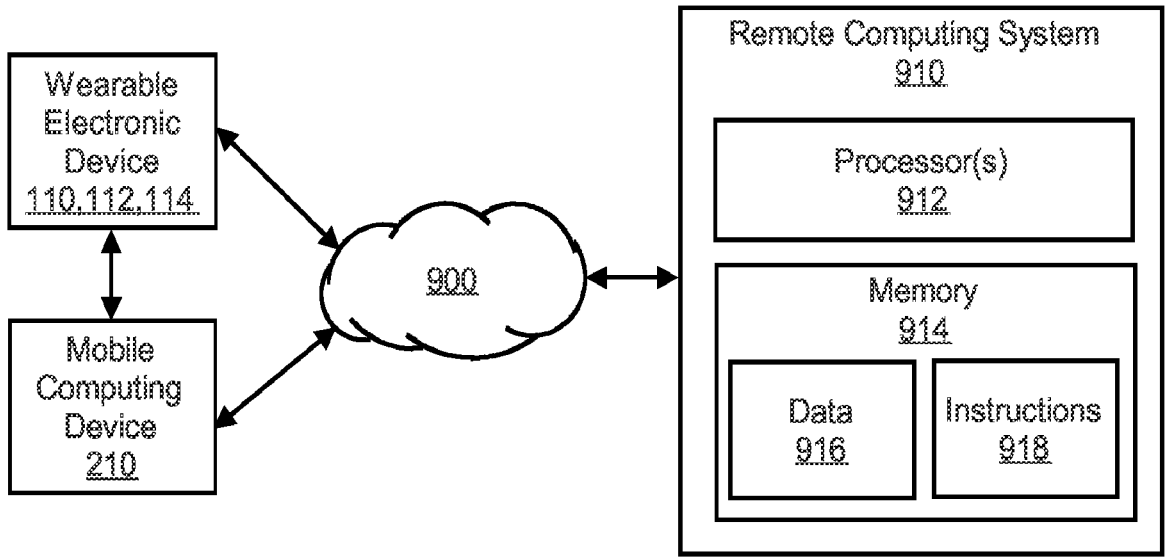
FIG. 10 depicts a computing system according to some implementations of the present disclosure.

Referring now to FIG. 10, the wearable computing device 110, 112, 114 can be communicatively coupled to a network 900. The wearable computing device 110, 112, 114 can communicate data (e.g., motion data) over the network 900 to a remote computing system 910 (e.g., internet-of-things device) for storage and/or processing. For instance, in some embodiments, the wearable computing device 110, 112, 114 can communicate the data to mobile computing device 210. In such embodiments, the wearable computing device 110, 112, 114 can communicate the data to the mobile computing device 210 and then the mobile computing device 210 can communicate the data over the network 900 to the remote computing system 910. In alternative embodiments, the wearable computing device 110, 112, 114 can bypass the mobile computing device 210 and instead communicate the data directly to the remote computing system 910 via the network 900.

The remote computing system 910 includes one or more processors 912 and a memory 914. The one or more processors 912 can be any suitable processing device (e.g., a processor core, a microprocessor, an ASIC, an FPGA, a controller, a microcontroller, etc.) and can be one processor or a plurality of processors that are operatively connected. The memory 914 can include one or more non-transitory computer-readable storage media, such as RAM, ROM, EEPROM, EPROM, flash memory devices, magnetic disks, etc., and combinations thereof. The memory 914 can store data 916 and instructions 918 which are executed by the processor 912 to cause the remote computing system 910 to perform operations, such as any of the operations described herein. For instance, in some implementations, the memory 914 of the remote computing system 910 can be configured to store the one or more machine-learned models 320 discussed above with reference to FIG. 3. In this manner, the data obtained from one or more sensors (e.g., accelerometer, gyroscope, barometer, etc.) onboard the wearable computing device 110, 112, 114 and indicative of the user engaging in a fall risk activity can be communicated to the remote computing system 910 and provided as an input to the one or more machine-learned models 320 stored in the memory 914 thereof. The one or more machine-learned models 320 can be configured to process the data and output an adjusted fall detection threshold. Furthermore, the adjusted fall detection threshold can be communicated over the network 900 to the wearable computing device 110, 112, 114. In this manner, the fall detection threshold can be adjusted while the user wearing the wearable computing device 110, 112, 114 is engaging in the fall risk activity.

In some embodiments, the remote computing system 910 includes or is otherwise implemented by one or more computing devices. In instances in which the remote computing system 910 includes plural server computing devices, such server computing devices can operate according to sequential computing architectures, parallel computing architectures, or some combination thereof.

The network 900 can be any type of communications network, such as a local area network (e.g., intranet), wide area network (e.g., Internet), or some combination thereof and can include any number of wired or wireless links. In general, communication over the network 900 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

The technology discussed herein refers to sensors and other computer-based systems, as well as actions taken, and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computer-implemented method for assessing a fall risk of a user, the computer-implemented method comprising:

obtaining, by one or more processors, data indicative of the user engaging in an increased risk of falling from one or more sensors of a wearable computing device worn by the user, wherein the data indicative of the user engaging in an increased risk of falling comprises at least one of the user standing up and walking too fast after sleeping, the user carrying an object while walking, or the user being distracted while walking;

adjusting, by the one or more processors, a sensitivity of a fall detection threshold of the wearable computing device worn by the user based, at least in part, on the increased risk of falling, wherein adjusting the sensitivity of the fall detection threshold of the wearable computing device comprises:

providing, by the one or more processors, the data indicative of the user engaging in the increased risk of falling from the one or more sensors as an input to a machine-learned model configured to process the data to determine an adjusted fall detection threshold; and obtaining, by the one or more processors, the adjusted fall detection threshold as an output of the machine-learned model; and providing, by the one or more processors, a notification to the user based on the increased risk of falling.

2. The computer-implemented method of claim 1, wherein obtaining data indicative of the user engaging in the increased risk of falling comprises obtaining, by the one or more processors, a signal from a mobile computing device associated with the user, the signal indicative of the user engaging in the increased risk of falling.

3. The computer-implemented method of claim 2, wherein providing the notification comprises providing, by the one or more processors, the notification for display on a display screen of the mobile computing device.

4. The computer-implemented method of claim 1, wherein:

the one or more sensors of the wearable computing device includes a plurality of different sensors; and the adjusted fall detection threshold includes a plurality of adjusted fall detection thresholds, each of the plurality of adjusted fall detection thresholds associated with a respective sensor of the plurality of different sensors.

5. The computer-implemented method of claim 1, further comprising:

obtaining, by the one or more processors, sleep data associated with a sleep event.

6. The computer-implemented method of claim 5, wherein adjusting the sensitivity of the fall detection threshold of the wearable computing device comprises adjusting, by the one or more processors, the sensitivity of the fall detection threshold of the wearable computing device according to the sleep data and the data indicative of the user engaging in an increased risk of falling.

7. The computer-implemented method of claim 6, wherein the sleep data comprises at least one of a duration of the sleep event or a depth of the sleep event.

8. The computer-implemented method of claim 7, wherein the depth of the sleep event comprises data indicative of whether the user is waking from a rapid-eye-movement (REM) sleep cycle or a non-REM sleep cycle.

9. The computer-implemented method of claim 1, wherein obtaining data indicative of the user engaging in the increased risk of falling includes:

obtaining, by the one or more processors, first data from one or more sensors of a first wearable computing device worn at a first location on a body of the user; and obtaining, by the one or more processors, second data from one or more sensors of a second wearable computing device worn at a second location on the body of the user, the second location being different than the first location.

10. The computer-implemented method of claim 9, wherein adjusting the sensitivity of the fall detection threshold of the wearable computing device comprises adjusting, by the one or more processors, the sensitivity of the fall detection threshold of at least one of the first wearable computing device or the second wearable computing device.

11. A wearable computing device comprising:

a plurality of sensors; and one or more processors communicatively coupled with the plurality of sensors, the one or more processors configured to:

obtain data indicative of a user wearing the wearable computing device engaging in an increased risk of falling from the plurality of sensors of the wearable computing device worn by a user, wherein the data indicative of the user engaging in an increased risk of falling comprises at least one of the user standing up and walking too fast after sleeping, the user carrying an object while walking, or the user being distracted while walking;

adjust a sensitivity of a fall detection threshold based, at least in part, on the increased risk of falling, wherein, to adjust the sensitivity of the fall detection threshold, the one or more processors are configured to:

provide the data indicative of the user wearing the wearable computing device engaging in the increased risk of falling as an input to a machine-learned model; and obtain an adjusted fall detection threshold as an output of the machine-learned model; and provide a notification to the user based on the increased risk for falling.

12. The wearable computing device of claim 11, wherein to obtain data indicative of the user engaging in the increased risk of falling, the one or more processors are configured to:

provide data from one or more sensors of the plurality of sensors as an input to a machine-learned model configured to classify the data from the plurality of sensors as corresponding to a first fall risk activity of a plurality of different fall risk activities; and obtain an identifier indicative of the first fall risk activity as an output of the machine-learned model.

13. The wearable computing device of claim 11, wherein the plurality of sensors include at least one of an accelerometer, a gyroscope, or a barometer.

14. The wearable computing device of claim 11, further comprising:

one or more output devices configured to output the notification to the user based on the increased risk for falling.

15. The wearable computing device of claim 14, wherein the one or more output devices comprise at least one of a speaker or a display screen.

16. A non-transitory computer-readable medium storing instructions that, when executed by one or more processors, cause the one or more processors to perform operations, the operations comprising:

obtaining data indicative of a user engaging in an increased risk of falling from one or more sensors of a wearable computing device worn by a user, wherein the data indicative of the user engaging in an increased risk of falling comprises at least one of the user standing up and walking too fast after sleeping, the user carrying an object while walking, or the user being distracted while walking;

adjusting a sensitivity of a fall detection threshold based, at least in part, on the increased risk of falling, wherein adjusting the sensitivity of the fall detection threshold comprises providing the data indicative of the user engaging in an increased risk of falling from the one or more sensors as an input to a machine-learned model and obtaining an adjusted fall detection threshold as an output of the machine-learned model; and providing a notification to the user based on the increased risk of falling.

* * * * *